United States Patent
Funke et al.

(10) Patent No.: US 7,256,313 B2
(45) Date of Patent: Aug. 14, 2007

(54) METHOD FOR THE PRODUCTION OF ISOPHORONDIAMINE (IPDA, 3-AMINOMETHYL-3,5,5-TRIMETHYL-CYCLOHEXYLAMINE) HAVING A HIGH CIS/TRAN-ISOMER RATIO

(75) Inventors: Frank Funke, Ludwigshafen (DE); Thomas Hill, Ludwigshafen (DE); Jobst Rüdiger Von Watzdorf, Mannheim (DE); Wolfgang Mattmann, Limburgerhorf (DE); Wolfgang Harder, Weinheim (DE); Erhard Henkes, Einhausen (DE); Gerd Littmann, Weinheim (DE); Manfred Julius, Limburgerhof (DE)

(73) Assignee: BASF Aktiengesellschaft (DE)

( * ) Notice: Subject to any disclaimer, the term of this patent is extended or adjusted under 35 U.S.C. 154(b) by 283 days.

(21) Appl. No.: 10/522,994

(22) PCT Filed: Aug. 6, 2003

(86) PCT No.: PCT/EP03/08722

§ 371 (c)(1),
(2), (4) Date: Feb. 2, 2005

(87) PCT Pub. No.: WO2004/020386

PCT Pub. Date: Mar. 11, 2004

(65) Prior Publication Data

US 2005/0245767 A1    Nov. 3, 2005

(30) Foreign Application Priority Data

Aug. 9, 2002 (DE) ................. 102 36 675

(51) Int. Cl.
  C07C 209/84 (2006.01)
  C07C 209/86 (2006.01)
  C07C 209/88 (2006.01)
(52) U.S. Cl. ............. 564/448; 564/302; 564/303; 564/444
(58) Field of Classification Search ............. None
  See application file for complete search history.

(56) References Cited

U.S. PATENT DOCUMENTS

| | | |
|---|---|---|
| 5,504,254 A | 4/1996 | Haas et al. |
| 5,583,260 A | 12/1996 | Haas et al. |
| 5,756,845 A | 5/1998 | Voit et al. |
| 6,022,999 A | 2/2000 | Voit et al. |
| 2004/0225156 A1 | 11/2004 | Funke et al. |

FOREIGN PATENT DOCUMENTS

DE    4211454 A    6/1992

*Primary Examiner*—Brian Davis
(74) *Attorney, Agent, or Firm*—Connolly Bove Lodge & Hutz LLP (57) ABSTRACT

The invention relates to processes for preparing 3-aminomethyl-3,5,5-trimethylcyclo-hexylamine (isophoronediamine, IPDA) having a high cis/trans isomer ratio. IPDA having a cis/trans isomer ratio in the range from 63/37 to 66/34 can be obtained in any desired cis/trans isomer ratio, irrespective of temperature, by reacting IPDA with $H_2$ and $NH_3$ in the presence of a hydrogenation catalyst. IPDA having a cis/trans isomer ratio of at least 73/27 which is an important starting material for the synthesis of polyurethanes and polyamides can be obtained by combining this isomerization process with distillative processes.

20 Claims, 4 Drawing Sheets

METHOD FOR THE PRODUCTION OF ISOPHORONDIAMINE (IPDA, 3-AMINOMETHYL-3,5,5-TRIMETHYL-CYCLOHEXYLAMINE) HAVING A HIGH CIS/TRAN-ISOMER RATIO

CROSS-REFERENCE TO RELATED APPLICATIONS

This application is a National Stage of PCT/EP2003/008722 filed Aug. 6, 2003, which in turn claims priority over DE 102 36 675.6 filed in Germany Aug. 9, 2002.

BACKGROUND

1. Technical Field

The invention relates to processes for preparing 3-aminomethyl-3,5,5-trimethylcyclo-hexylamine (isophoronediamine, IPDA) having a high cis/trans isomer ratio.

2. Discussion of the Background

IPDA is used as a starting product for preparing isophorone diisocyanate (IPDI), an isocyanate component for polyurethane systems, as an amine component for polyamides and as a hardener for epoxy resins. IPDA is customarily prepared from 3-cyano-3,5,5-trimethylcyclohexanone (isophoronenitrile, IPN) by converting the carbonyl group to an amino group and the nitrile group to an aminomethyl group in the presence of ammonia, hydrogen and customary hydrogenation catalysts. Mixtures of cis-IPDA and trans-IPDA are obtained. The two isomers have differing reactivities, which is of significance for the intended technical application. According to DE-A 42 11 454, the use of an IPDA isomer mixture consisting of above 40% of the trans-isomer and below 60% of the cis-isomer as a reaction component in polyaddition resins, in particular epoxy resins, both lengthens the pot life and reduces the maximum curing temperature. Conversely, to achieve a very high reaction rate, preference is given to IPDA isomer mixtures which have a very high cis-isomer content ($\geq 70\%$). Commercially obtainable IPDA therefore has a cis/trans isomer ratio of 75/25.

Various processes for achieving a high cis/trans or a high trans/cis ratio are already known from the prior art.

According to DE-A 43 43 890, the animating hydrogenation of IPN to IPDA is effected by allowing a mixture of IPN, ammonia and a $C_1$-$C_3$-alcohol to trickle through a trickle bed reactor equipped with a cobalt and/or ruthenium fixed bed catalyst in the presence of hydrogen at from 3 to 8 MPa and a temperature of from 40 to 150° C., preferably from 90 to 130° C., and distillatively working up the reaction mixture to remove $NH_3$, $H_2O$ and by-products. When an Ru supported catalyst is used, high cis/trans isomer ratios of 84/16 (total yield of IPDA: 81%) are achieved.

DE-A 43 43 891 describes a process for preparing IPDA by reacting IPN with hydrogen in the presence of ammonia and a suspension or fixed bed hydrogenation catalyst from the group of cobalt, nickel and noble metal catalysts at a pressure of from 3 to 20 MPa and a temperature of up to 150° C., and distillatively working up the reaction mixture. The reaction is carried out in two stages, and precisely defined temperature ranges have to be observed for the individual stages. A cis/trans isomer ratio of 80/20 can be achieved at an overall IPDA yield of 91.9%.

In the process of EP-A 0 926 130, the hydrogenation is carried out in the presence of an acid over catalysts which comprise copper and/or a metal of the eighth transition group of the periodic table. Both Lewis and Brönstedt acids are used; preference is given to using 2-ethylhexanoic acid. The addition of acid increases the cis/trans isomer ratio. The cis/trans isomer ratios are generally $\geq 70/30$ at an overall IPDA yield of $\geq 90\%$.

The process of EP-B 0 729 937 is notable in that the process is carried out in three spatially separated reaction chambers using cobalt, nickel, ruthenium and/or other noble metal catalysts. Upstream of the second reactor, aqueous NaOH solution is metered in, which reduces the formation of cyclic by-products such as 1.3.3-trimethyl-6-azabicyclo [3.2.1]octane.

In the process of DE-A 101 42 635.6, which has an earlier priority date but was unpublished at the priority date of the present invention, IPDA having a cis/trans isomer ratio of at least 70/30 is obtained, starting from IPN, by using a hydrogenation catalyst in the hydrogenation step which has an alkali metal content of $\leq 0.03\%$ by weight, calculated as the alkali metal oxide.

A disadvantage of the existing processes for preparing IPDA having a high cis content is the costly and inconvenient preparation of the catalysts used. In addition, these catalysts generally suffer from aging, which reduces their catalytic activity in the course of time. In order to compensate for this, the reaction temperature is usually increased, which leads, however, to a deterioration in the cis/trans isomer ratio and the selectivity and therefore to an increase in the formation of by-products. In addition, most of the processes known from the prior art are notable for a complicated reaction procedure.

A process for preparing isophoronediamine having a high trans/cis isomer ratio can be taken from DE-A 42 11 454. In this process, trans-isophoronediamine is prepared from isophoronenitrile via isophoronenitrile azine. It is also described that trans-isophoronediamine would be obtained by distilling the commercially obtainable cis/trans isomer mixture. However, since the cis-isomer occurs as the main product, this process is uneconomic.

SUMMARY

It is an object of the present invention to provide a process for preparing isophoronediamine (IPDA) having a cis/trans isomer ratio of at least 73/27 which avoids the disadvantages of the prior art.

We have found that this object is achieved by a process for preparing substantially pure 3-aminomethyl-3,5,5-trimethylcyclohexylamine (isophoronediamine, IPDA) having a cis/trans isomer ratio of at least 73/27, comprising the following steps:

a) providing crude IPDA having a cis/trans isomer ratio of <73/27;

b) purifying and separating the crude IPDA into a fraction having a cis/trans isomer ratio of at least 73/27 and a fraction having a cis/trans isomer ratio of less than 63/37;

c) isomerizing the fraction of substantially pure IPDA having a cis/trans isomer ratio of less than 63/37 obtained in step b) to IPDA having a cis/trans isomer ratio in the range from 63/37 to 66/34 in the presence of $H_2$, $NH_3$ and a hydrogenation catalyst and recycling it into step a) of the process.

BEST AND VARIOUS MODES FOR CARRYING OUT THE DISCLOSURE

A more complete appreciation of the disclosure and many of the attendant advantages will be readily obtained, as the same becomes better understood by reference to the following detailed description when considered in connection with the accompanying drawings.

Starting from IPDA having any desired cis/trans isomer ratio <73/27, the process according to the invention allows IPDA having a cis/trans isomer ratio of ≧73/27 to be obtained. The process therefore remains economical even when aging of the catalyst and an associated increase in the reaction temperature reduce the cis content in the crude IPDA in the course of time. Since the process according to the invention is independent of such influences, it is superior to those processes which prepare IPDA having a high cis/trans isomer ratio by using special catalysts which are usually expensive to prepare and complex. However, irrespective of this, the process according to the invention can also be combined with such more complicated synthetic processes. It is more economical to prepare the IPDA using inexpensive catalysts and accept a worse cis/trans isomer ratio of the crude IPDA.

"Substantially pure" IPDA is IPDA in which the fraction of impurities is less than 2% by weight, preferably less than 1% by weight, more preferably less than 0.3% by weight.

The process according to the invention is preferably used to obtain IPDA having a cis/trans isomer ratio in the range from 73/27 to 76/24, more preferably having a cis/trans isomer ratio in the range from 73/27 to 75/25. (See also discussion, step b).)

The individual steps of the process are now illustrated.

Step a)

In general, any product mixture, known as crude IPDA, which results from a process for preparing IPDA may be used. "Crude IPDA" means that the product mixture contains at least 88% by weight of IPDA, preferably at least 92% by weight of IPDA, more preferably at least 95% by weight of IPDA.

Since IPDA having a cis/trans isomer ratio of at least 73/27 is to be obtained, it is economically only viable to use product mixtures which contain IPDA having a cis/trans isomer ratio of less than 73/27. Since it is possible to prepare IPDA having a cis/trans isomer ratio of less than 70/30 using aging catalysts and without complicated process operation, the process according to the invention is particularly economical when IPDA having a cis/trans isomer ratio of less than 70/30 is used. It is also possible to use product mixtures which contain IPDA having a cis/trans isomer ratio greater than 73/27, in order to still further enrich the cis-isomer by distillation.

Step b)

The product mixture provided in step a) can be purified and separated either by distillation or by crystallization.

cis-IPDA (having a purity of 98.9%) has a boiling point under atmospheric pressure of 253.4° C. and a melting point of 22° C., while trans-IPDA (having a purity of 98.4%) has a boiling point under atmospheric pressure of 250.7° C. and a melting point of −34.6° C. Although there is a greater difference in the melting point of the two isomers than between their boiling points, preference is given to purification and separation by distillation for reasons of cost.

This purification and separation of the crude IPDA by distillation may be carried out in any desired distillation column. Preference is given to effecting distillation in at least 2 spatially separated columns. Particular preference is given to using at least one dividing wall column.

The distillation of the product mixture (crude IPDA) usually removes $NH_3$, and also low-and high-boiling components, for example the products by-produced in the preparation of IPDA from IPN, such as HCN elimination products, methylated by-products and/or incompletely hydrogenated secondary products via the top or bottom of the column.

For the purposes of the invention, low-boiling components/impurities are components/impurities which have lower boiling points than cis- and trans-IPDA, and high-boiling components/impurities are those which have higher boiling points than cis- and trans-IPDA.

A separation into a cis-isomer-enriched fraction and a cis-isomer-depleted (and therefore trans-isomer-enriched) fraction is also effected.

The cis-enriched fraction of the IPDA has a cis/trans isomer ratio of at least 73/27, preferably a cis/trans isomer ratio in the range from 73/27 to 76/24, more preferably a cis/trans isomer ratio in the range from 73/27 to 75/25.

The cis-depleted fraction of the IPDA has a cis/trans isomer ratio of less than 63/37, preferably ≦60/40, more preferably ≦58/42. The cis-isomer-enriched fraction is commercially desirable. The cis-isomer-depleted fraction can likewise be commercially utilized (see DE-A 42 11 454).

When one column is used for the distillation, it is generally operated at bottom temperatures of from 150 to 300° C., preferably from 170 to 250° C., more preferably from 170 to 185° C., and top temperatures of from 5 to 100° C., preferably from 10 to 90° C., more preferably from 15 to 65° C. The pressure in the column is generally from 10 to 2000 mbar, preferably from 20 to 200 mbar, more preferably from 35 to 50 mbar.

When two columns are used for the distillation, the first column is generally operated at bottom temperatures of from 150 to 300° C., preferably from 170 to 250° C., more preferably from 170 to 195° C., and top temperatures of from 5 to 100° C., preferably from 10 to 90° C., more preferably from 15 to 65° C. The pressure in the first column is generally from 10 to 1000 mbar, preferably from 30 to 500 mbar, more preferably from 35 to 200 mbar. The second column is generally operated at bottom temperatures of from 140 to 300° C., preferably from 150 to 250° C., more preferably from 160 to 195° C., and top temperatures of from 100 to 250° C., preferably from 130 to 200° C., more preferably from 140 to 170° C. The pressure in the second column is generally from 10 to 1000 mbar, preferably from 30 to 300 mbar, more preferably from 35 to 120 mbar.

The column(s) generally has/have a total separating performance of at least 20 theoretical plates, preferably of at least 30 theoretical plates, more preferably of at least 40 theoretical plates.

The columns may each have different internals. Examples of such internals include random packings such as Pall rings and Raschig rings, structured sheet metal packings such as Mellapak 250Y® from Sulzer Ltd. (Winterthur/Switzerland), from Montz (Hilden/Germany) and from Koch-Glitsch (Wichita, Kans./USA) and structured woven metal packings such as Sulzer BX® from Sulzer Ltd. (Winterthur/Switzerland), from Montz (Hilden/Germany) and from Koch-Glitsch (Wichita, Kans./USA).

Step c)

According to the invention, the cis-isomer-depleted fraction is recycled into step a) of the process after isomerization. This isomerization step, i.e. passing of IPDA having any desired cis/trans isomer ratio over a hydrogenation catalyst in the presence of $H_2$ and $NH_3$ resulting, irrespective of temperature, in a thermodynamic equilibrium having a cis/trans isomer ratio in the range from 63/37 to 66/34, preferably from 64/36 to 66/36, more preferably from 64/36 to 65/35, is not known from the prior art.

The invention therefore likewise provides a process for preparing 3-aminomethyl-3,5,5-trimethylcyclohexylamine (isophoronediamine, IPDA) having a cis/trans isomer ratio in the range from 63/37 to 66/34 by reacting IPDA having a cis/trans isomer ratio of less than 63/37 with $H_2$ and $NH_3$ over a hydrogenation catalyst.

Although the isomerization of IPDA having a cis/trans isomer ratio of greater than 63/37 is possible, it would make no economic sense when the primary objective is to increase the cis-content in the cis/trans isomer mixture.

The isomerization of IPDA having a cis/trans isomer ratio of less than 63/37 to IPDA having a cis/trans isomer ratio in the range from 63/37 to 66/34 is generally carried out at temperatures of from 70 to 200° C., preferably from 80 to 150° C., more preferably from 90 to 130° C., and pressures of from 10 to 300 bar, preferably from 50 to 250 bar, more preferably from 100 to 240 bar. The reaction duration is dependent upon the isomerization temperature and the catalyst used.

In the process according to the invention for isomerizing IPDA, useful hydrogenation catalysts are in principle any common hydrogenation catalysts, preferably those which contain at least one transition metal selected from the group of copper, silver, gold, iron, cobalt, nickel, rhenium, ruthenium, rhodium, palladium, osmium, iridium, platinum, chromium, molybdenum and tungsten, each in metallic form (oxidation state 0) or in the form of compounds, for example oxides, which are reduced to the corresponding metal under the process conditions.

Among these hydrogenation catalysts, particular preference is given to those which comprise at least one transition metal selected from the group of copper, silver, iron, cobalt, nickel, ruthenium, rhodium, palladium, osmium, iridium and platinum, each in metallic form (oxidation state 0) or in the form of compounds, for example oxides, which are reduced to the corresponding metal under the process conditions.

Very particular preference is given to hydrogenation catalysts which comprise at least one transition metal selected from the group of copper, cobalt, nickel, ruthenium, iridium, rhodium, palladium and platinum, each in metallic form (oxidation state 0) or in the form of compounds, for example oxides, which are reduced to the corresponding metal under the process conditions.

Greatest preference is given to hydrogenation catalysts which comprise a transition metal selected from the group of cobalt and ruthenium, each in metallic form (oxidation state 0) or in the form of compounds, for example oxides, which are reduced to the corresponding metal under the process conditions.

When the catalytically active transition metals are applied to supports (selected from the group of aluminum oxide ($Al_2O_3$), zirconium dioxide ($ZrO_2$), titanium dioxide ($TiO_2$), carbon and/or oxygen-containing compounds of silicon, calculated as $SiO_2$), these catalysts generally comprise a total, based on the total weight of the catalyst, of from 20 to 99.9% by weight, preferably from 30 to 99.9% by weight, more preferably from 40 to 99.9% by weight, of support, and from 0.1 to 80% by weight, preferably from 0.1 to 70% by weight, more preferably from 0.1 to 60% by weight, of transition metal, calculated as the metal in the oxidation state 0.

During the isomerization, a catalyst hourly space velocity of from 0.1 to 2 kg, preferably from 0.2 to 1.5 kg, more preferably from 0.4 to 1 kg, of IPDA having a cis/trans isomer ratio of less than 63/37 per l of catalyst and hour is maintained.

Preference is given to carrying out the isomerization in liquid ammonia. For every mole of IPDA having a cis/trans isomer ratio of less than 63/37, it is advantageous to use an excess of $NH_3$ in the isomerization of from 0.5 to 100 mol, preferably from 2 to 50 mol, more preferably from 5 to 40 mol.

The isomerization of the IPDA may be carried out in the presence of a solvent, for example alkanols or ethers (tetrahydrofuran), although it is also possible to work without a solvent.

The isomerization can be carried out either continuously or batchwise. Preference is given to the continuous reaction. It is possible to use any desired pressure-resistant stirred tanks or stirred tank batteries. In a particularly preferred embodiment, reactors are used in which the IPDA having a cis/trans isomer ratio of less than 63/37 is continuously passed over a fixed catalyst bed by the liquid phase or trickle method. It is also possible to use shaft furnaces.

In another implementation variant of the isomerization process according to the invention, the isomerization is not carried out in a separate stirred tank under the conditions specified above, but instead the IPDA having a cis/trans isomer ratio of <63/37 to be isomerized is fed to any desired reaction known from the prior art for preparing IPDA from IPN, $H_2$ and $NH_3$ in the presence of a hydrogenation catalyst. Examples of IPDA preparation processes from the prior art are given in the introduction.

Figure 1:
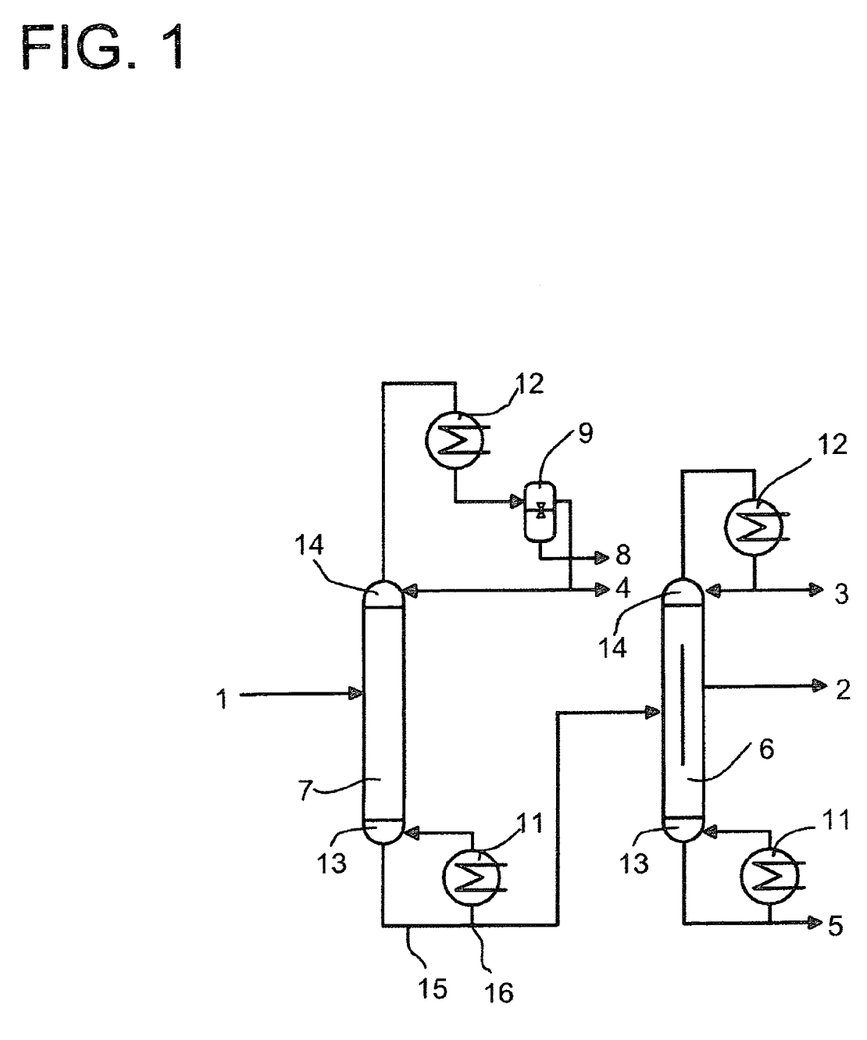
FIG. 1 is a schematic plant illustration of two distillation columns, in which crude IPDA is initially introduced into a conventional distillation column.
Figure 2:
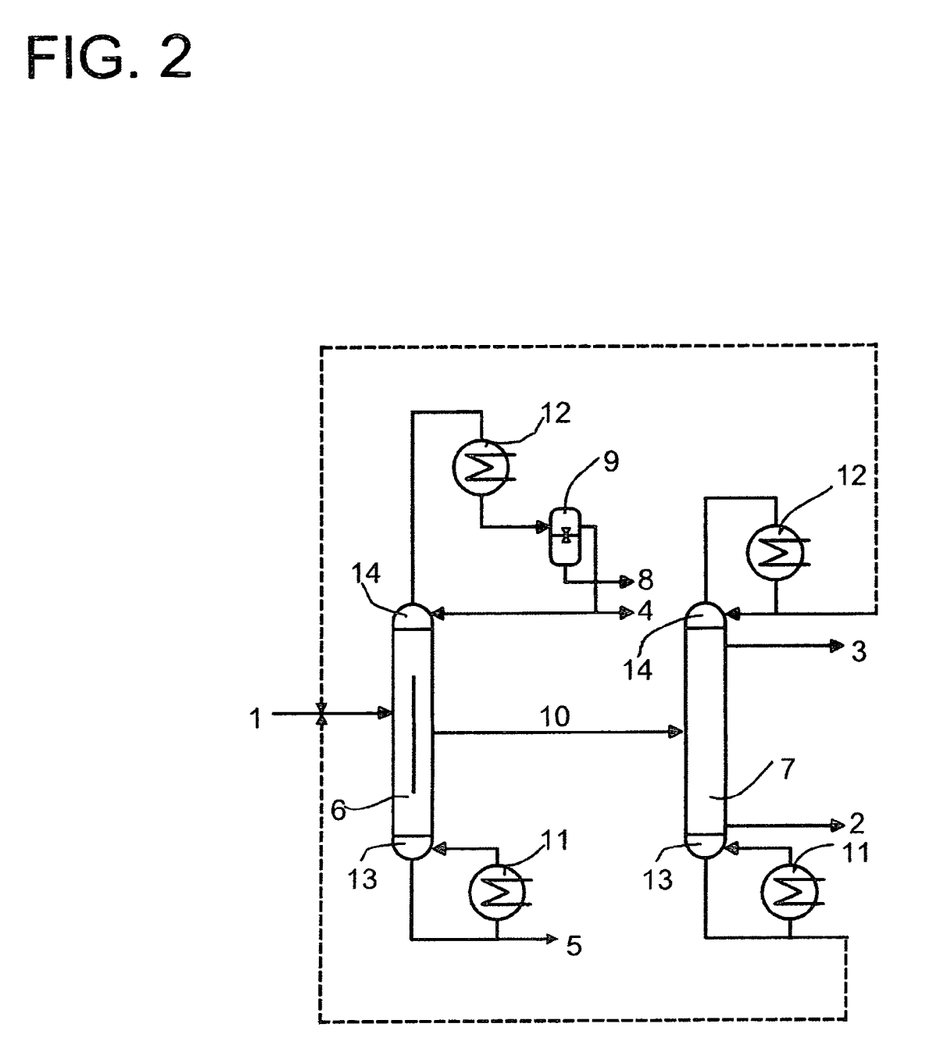
FIG. 2 is a schematic plant illustration of two distillation columns, in which crude IPDA is initially introduced into a dividing wall distillation column.

FIGS. 1 and 2 of the appended drawing show schematic plants in which step b) of the process according to the invention for obtaining IPDA having a cis/trans isomer ratio of at least 73/27 is carried out in two columns, i.e.

FIG. 1 is a schematic depiction of a plant in which the first column is a conventional distillation column and the second column is a dividing wall column.

FIG. 2 is a schematic depiction of a plant where the first column is a dividing wall column and the second column is a conventional distillation column.

In a plant according to FIG. 1, a product mixture containing crude IPDA is introduced into a conventional distillation column 7 via an inlet 1 and is distilled there. Low-boiling components are removed via the top 14 of the column, transferred after condensation in a condenser 12 to a phase separator 9 and separated there into a lighter organic and a heavier aqueous phase. The lighter organic phase is partially discarded via the takeoff 4, partially recycled into the distillation column 7. The heavier aqueous phase is disposed of via the outlet 8.

The temperatures at the top of the distillation column 7 are generally from 20 to 100° C., preferably from 30 to 80° C. and more preferably from 35 to 65° C., at an average pressure in the column of from 50 to 1000 mbar. The temperatures at the bottom of the distillation column 7 are generally from 150 to 250° C., preferably from 170 to 225° C., more preferably from 170 to 190° C. Preference is given to an average pressure in the column of from 100 to 500 mbar, particular preference to an average pressure of from 110 to 200 mbar.

The bottoms 13 of the distillation column 7 are transferred continuously to a dividing wall column 6. In line 15, a branch 16 leads to an evaporator 11 where a portion of the bottom effluent is evaporated again and fed back into column 7. The cis-isomer-enriched fraction is withdrawn from column 6 via a sidestream takeoff 2, and the trans-isomer-enriched fraction is removed via the top of the distillation column, condensed in a condenser 12 and then partially recycled into column 6, partially withdrawn via line 3. After isomerization, and the associated increase in the cis content, the fraction isomerized in this way is fed into line 1. High-boiling impurities are removed via the bottom 13 of the dividing wall column 6 and partially discharged via line 5, partially fed back to column 6 after evaporation in an evaporator 11.

The dividing wall column 6 is generally operated at temperatures of from 100 to 250° C. at the top and temperatures of from 150 to 300° C. at the bottom, and pressures from 10 to 1000 mbar, preferably at temperatures of from 130 to 190° C. at the top and/or temperatures of from 170 to 250° C. at the bottom and/or pressures of from 30 to 200 mbar, more preferably at temperatures of from 140 to 160° C. at the top and/or temperatures of from 170 to 195° C. at the bottom and/or pressures of from 35 to 50 mbar.

When step b) of the process according to the invention is carried out in a plant according to FIG. 2, the crude IPDA is introduced into a dividing wall column 6 via the feed 1. High-boiling impurities obtained as the bottoms 13 of the column are partially discharged via the outlet 5, partially fed back to the column after evaporation in an evaporator 11. Low-boiling impurities are removed via the top 14 of the column and transferred after condensation in a condenser 12 to a phase separator 9. The lighter organic phase which collects is partially discharged via the outlet 4, partially recycled into the dividing wall column 6. The heavier phase is discharged via the outlet 8.

The purified IPDA is withdrawn via a sidestream takeoff 10 of the dividing wall column 6 and transferred to a further column 7 which in this case is configured as a conventional distillation column. The lowest-boiling components are removed via the top 14 of the column 7 and, after condensation in a condenser 12, partially fed back to column 7, partially introduced into the inlet 1, in order to feed them to a renewed separation in column 6. The same happens to the highest-boiling components, which are removed via the bottom 13 of column 7 and partially fed back to column 7 after evaporation in an evaporator 11, partially added to the product mixture in inlet 1.

The cis-isomer-enriched fraction is removed via a sidestream takeoff 2, and the trans-isomer-enriched fraction via a sidestream takeoff 3 and, after isomerization, fed into line 1. The sidestream takeoff for the cis-isomer-enriched fraction is below the sidestream takeoff for the trans-isomer-enriched fraction.

It is particularly advantageous to carry out step b) of the process in a plant according to FIG. 2, since low- and high-boiling impurities are each removed at two points: low-boiling components are removed both via the top 14 of column 6 and via the top 14 of column 7, while high-boiling impurities are removed both via the bottom effluent 13 of column 6 and via the bottom effluent 13 of column 7.

In a plant according to FIG. 2, the dividing wall column 6 is generally operated at temperatures of from 5 to 100° C., preferably from 10 to 90° C., more preferably from 15 to 50° C. The temperatures at the bottom are generally from 150 to 300° C., preferably from 170 to 250° C., more preferably from 170 to 195° C. The average pressure in dividing wall column 6 is from 10 to 1000 mbar, preferably from 30 to 200 mbar, more preferably from 35 to 50 mbar. The temperatures at the top of the distillation column 7 are generally from 130 to 250° C., preferably from 140 to 200° C., more preferably from 150 to 170° C. The temperatures at the bottom of the distillation column 7 are generally from 140 to 250° C., preferably from 150 to 220° C., more preferably from 160 to 190° C. The average pressure in the distillation column 7 in a plant according to FIG. 2 is from 30 to 1000 mbar, preferably from 50 to 300 mbar, more preferably from 80 to 120 mbar.

EXAMPLES

The invention is now additionally illustrated in the implementation examples which follow.

Implementation Examples

Comparative Example 1

Preparation of IPDA from IPN and Subsequent Distillative Workup

The animating hydrogenation of isophoronenitrile to isophoronediamine is effected in a continuous process in three reactors connected in series at a pressure of 250 bar, as described in EP-B 0 729 937. The catalyst is heated up to 280° C. at a heating rate of 2K/min under a hydrogen atmosphere. After maintaining this temperature for 12 h, the temperature is returned to the particular reaction temperature.

Isophoronenitrile (130 ml/h), ammonia (600 g/h) and hydrogen (300 l/h) are passed at a temperature of from 80 to 100° C. by the liquid phase method through the first reactor (200 ml imination reactor), filled with $\gamma$-$Al_2O_3$ (4 mm extrudates) as a support for the catalyst. The imination is effected there. The reaction mixture is conducted into the first reactor with the catalyst described in EP-A 0 742 045. The temperature there is 90° C. In the last reactor (130° C.), the post-hydrogenation is effected over the same catalyst. The sequence is liquid phase-trickle-liquid phase. The product mixture is decompressed in a separator (composition see Table 1) and is distilled batchwise in a distillation column. Details of the distillation column: column diameter: 30 mm, packing height: 1.5 m, packing: Sulzer DX from Sulzer Ltd. (Winterthur, Switzerland), 45 theoretical plates, pressure 30 mbar, reflux ratio 10/1.

First, a fraction having a cis/trans isomer ratio of 60/40 is removed. The boiling point of this fraction is 137.5° C. Then, a fraction is isolated which contains 75% of cis-IPDA and 25% of trans-IPDA, and has a boiling point of 138.7° C. Samples taken are each analyzed by gas chromatography.

Example 2

Preparation of IPDA from IPN, Subsequent Distillative Workup and Recycling of the Cis-Depleted Fraction into the Synthesis Reactor Example 1 was repeated, except that 50 ml/h each of the first fraction removed (IPDA having a cis/trans isomer ratio of 60/40) are fed into the reaction in addition to the IPN stream (130 ml/h). Samples taken were analyzed by gas chromatography. The composition of the crude IPDA can be taken from Table 1.

TABLE 1

Results of Examples 1 and 2

| | Comparative Example 1 | Example 2 |
|---|---|---|
| Overall yield of IPDA | 92.8% | 94.4% |
| Cis/trans isomer ratio of the crude IPDA | 69.7% by weight | 66.1% by weight |
| By-products due to HCN elimination (Ia, Ib) | 4.4% by weight | 2.7% by weight |
| Methylated by-products (IIa, IIb) | 0.8% by weight | 0.4% by weight |
| Cyclic by-product 1,3,3-trimethyl-6-azabicyclo[3.2.1]octane (IV) | 0.3% by weight | 0.5% by weight |
| Aminonitrile (III) | 0% by weight | 0.1% by weight |
| Overall proportion of by-products in the crude IPDA | 5.5% by weight | 3.7% by weight |

The removal according to the invention of the cis-isomer-depleted IPDA fraction and its recycling into the synthesis reactor for isomerization allow the overall yield of IPDA to be still further increased and the proportion of by-products to be reduced. A slight increase in the proportion of compound IV is not detrimental, since this can easily be removed from IPDA. Despite the fact that the cis/trans isomer ratio becomes slightly worse, this procedure is more economical overall than the use of expensive catalysts and the observance of a complicated reaction sequence for preparing IPDA which has a higher cis/trans isomer ratio in the first place, since the cis-isomer can be enriched by the subsequent distillative process.

Example 3

Isomerization of Trans-IPDA

In a 300 ml autoclave equipped with a magnetic stirrer and catalyst basket, 20 ml of a cobalt catalyst prepared according to EP-A 0742 045 and 40 ml of trans-isophoronediamine were initially charged. The autoclave was sealed, and 60 ml of ammonia were injected via an inspection window. Hydrogen was used to adjust the pressure to 50 bar. After heating to a reaction temperature of 130° C., renewed injection of hydrogen was used to adjust the pressure to 250 bar. The autoclave was maintained under these conditions for 24 hours. After the end of the experiments, the autoclave was decompressed for 6 hours with stirring and at room temperature, in order to allow ammonia which was still dissolved to escape. For the gas chromatography analysis, pressurized samples were taken. The results are presented graphically in FIG. 3.

Example 4

Isomerization of Trans-IPDA

Example 3 was repeated, except that a reaction temperature of 110° C. instead of 130° C. was set. The results are presented graphically in FIG. 3.

Figure 3:
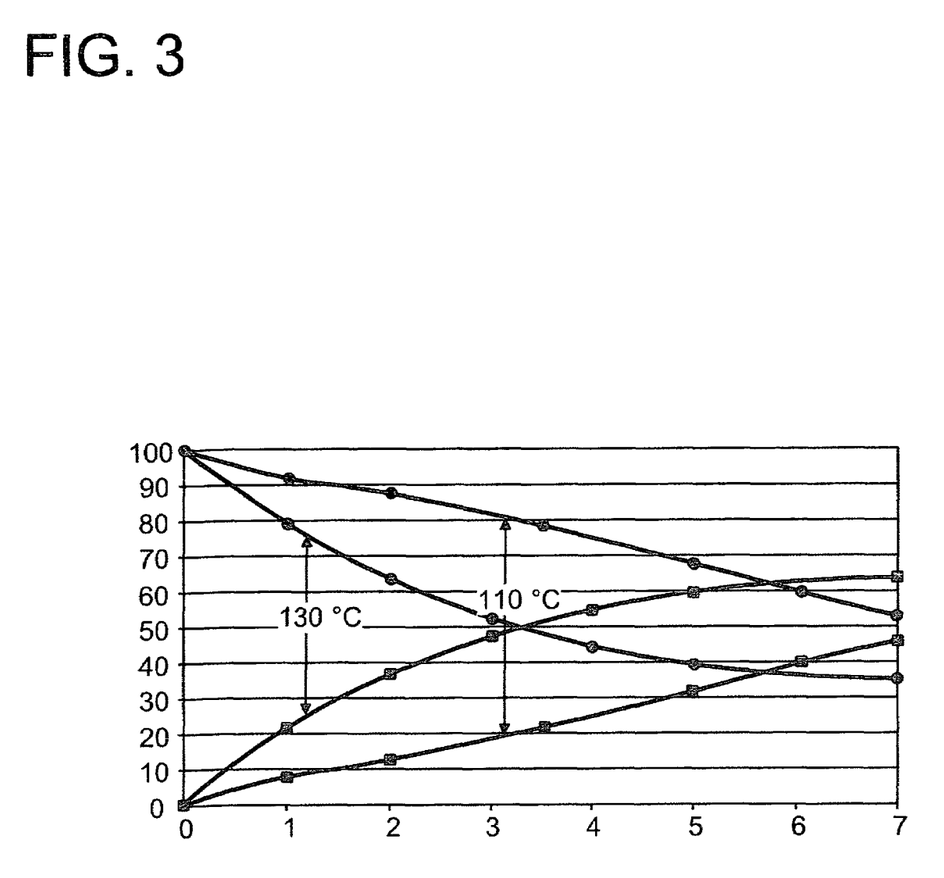
FIG. 3 illustrations a graphical evaluation of cis- and trans- isomers of IPDA from Examples 3 and 4.

Evaluation of FIG. 3

FIG. 3 shows the graphical evaluation of Implementation Examples 3 and 4. The y-axis shows the proportion of cis-IPDA in a cis-/trans-IPDA isomer mixture in % by weight. The reaction time in hours is plotted on the x-axis. cis-IPDA is represented by filled boxes, trans-IPDA by filled circles.

Starting from 100% by weight trans-IPDA, it can be seen that the proportion of the trans-isomer falls continuously in the course of time to a value of approx. 35% by weight, while the proportion of the cis-isomer increases continuously to a value of approx. 65% by weight. At a reaction temperature of 130° C., equilibrium has already been attained after 7 hours, while the reaction time is increased to 23 hours when the reaction temperature is reduced to 110° C. At 110° C., an isomer mixture having approx. 45% by weight of cis and approx. 55% by weight of trans is therefore obtained after 7 hours.

Example 5

Isomerization of cis-IPDA

In a 300 ml autoclave equipped with a magnetic stirrer and catalyst basket, 20 ml of cobalt catalyst prepared according to EP-A 0 742 045 and 40 ml of cis-IPDA were initially charged. The autoclave was sealed, and 60 ml of ammonia were injected via an inspection window. Hydrogen was used to adjust the pressure to 50 bar. After stepwise heating to a reaction temperature of 130° C., hydrogen was used to adjust the pressure to 250 bar. The autoclave was maintained under these conditions for 24 hours. After the end of the experiments, the autoclave was decompressed for 6 hours with stirring and at room temperature, in order to allow ammonia which was still dissolved to escape. For the gas chromatography analysis, pressurized samples were taken. The results are presented graphically in FIG. 4.

Example 6

Isomerization of cis-IPDA

Example 5 was repeated, except that a reaction temperature of 110° C. instead of 130° C. was set. The results are presented graphically in FIG. 4.

Example 7

Isomerization of cis-IPDA

Example 5 was repeated, except that a reaction temperature of 90° C. instead of 130° C. was set. The results can be taken from FIG. 4.

Figure 4:
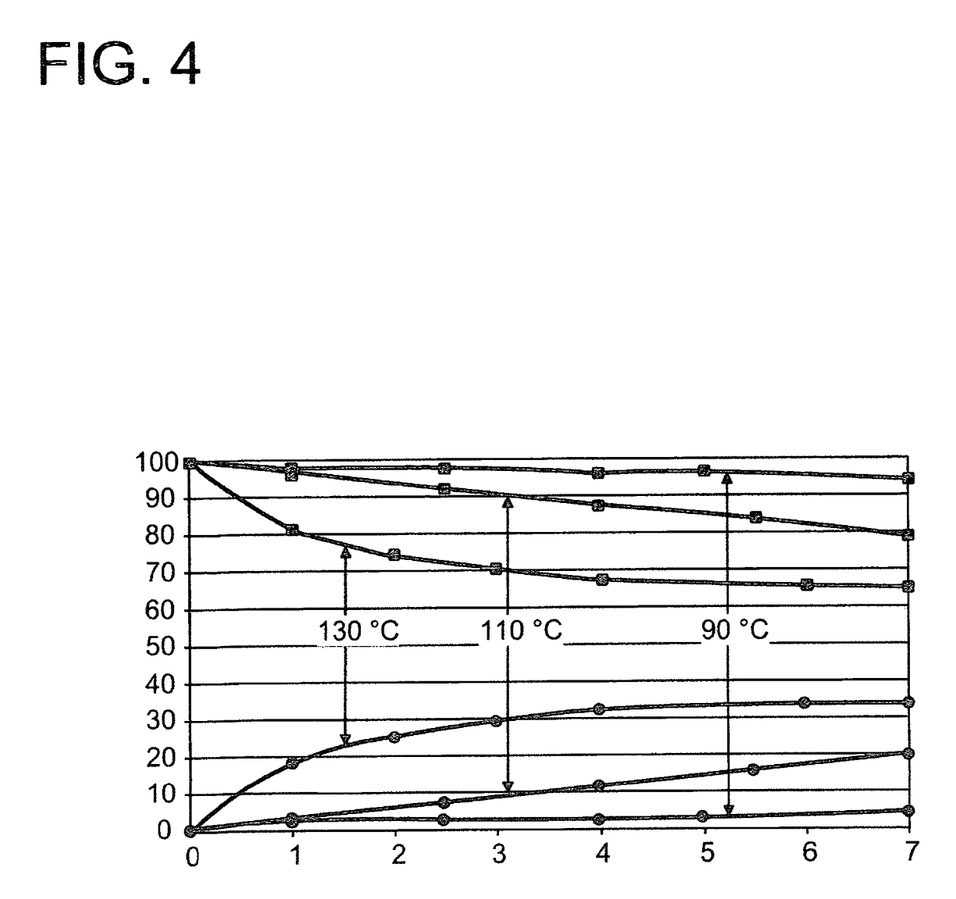
FIG. 4 illustrations a graphical evaluation of cis- and trans- isomers of IPDA from Examples 5, 6, and 7.

Evaluation of FIG. 4

FIG. 4 shows the graphical evaluation of Implementation Examples 5, 6 and 7. The reaction time in hours is plotted on the x-axis. The proportion of cis-IPDA in a cis-/trans-IPDA isomer mixture in % by weight is given on the y-axis. cis-IPDA is represented by filled boxes, trans-IPDA by filled circles.

Starting from 100% by weight of cis-IPDA, it can be seen that the proportion of the cis-isomer falls continuously with time to a value of approx. 65% by weight, while the proportion of the trans-isomer rises continuously to a value of approx. 35% by weight. Depending on the reaction temperature, equilibrium is attained with varying rapidity. At a reaction temperature of 130° C., equilibrium has already been attained after 7 hours, while reduction of the reaction temperature to 110° C. results in an increase in the reaction time to 22 hours, and further reduction of the reaction temperature to 90° C. results in 3 days being required.

Reference Numeral List

1 Feed of the crude IPDA
2 Takeoff for the cis-isomer-enriched fraction
3 Takeoff for the trans-isomer-enriched fraction
4 Takeoff for low-boiling impurities
5 Takeoff for high-boiling impurities
6 Dividing wall column
7 Conventional distillation column
8 Takeoff for the relatively heavy constituents of the low boiler fraction
9 Phase separator
10 Sidestream takeoff
11 Evaporator
12 Condenser
13 Bottom of the column
14 Top of the column
15 Line
16 Branch

We claim:

1. A process for preparing substantially pure 3-aminomethyl-3,5,5-trimethylcyclohexylamine (isophoronediamine, IPDA) having a cis/trans isomer ratio of at least 73/27, comprising the following steps:
  a) providing crude IPDA having a cis/trans isomer ratio of <73/27;
  b) purifying and separating, by distillation or by crystallization, the crude IPDA into a fraction having a cis/trans isomer ratio of at least 73/27 and a fraction having a cis/trans isomer ratio of less than 63/37;
  c) isomerizing the fraction of substantially pure IPDA having a cis/trans isomer ratio of less than 63/37 obtained in step b) to IPDA having a cis/trans isomer ratio in the range from 63/37 to 66/34 in the presence of $H_2$, $NH_3$ and a hydrogenation catalyst and recycling it into step a) of the process.

2. A process as claimed in claim 1, wherein the crude IPDA is purified and separated in step b) of the process by distillation.

3. A process as claimed in claim 2, wherein step b) of the process is carried out in two spatially separated distillation columns.

4. A process as claimed in claim 3, wherein at least one of the distillation columns is a diving wall column.

5. A process as claimed in claim 1, wherein the IPDA is separated in step b) of the process into a fraction having a cis/trans isomer ratio in the range from 73/27 to 76/24 and a fraction having a cis/trans isomer ratio of less than 63/37.

6. A process as claimed in claim 1, wherein crude IPDA having a cis/trans isomer ratio of $\leq 70/30$ is provided in step a) of the process.

7. A process as claimed in claim 1, wherein the hydrogenation catalyst used in step c) of the process is a catalyst comprising at least one transition metal selected from the group of copper, silver, gold, iron, cobalt, nickel, rhenium, ruthenium, rhodium, palladium, osmium, iridium, platinum, chromium, molybdenum and tungsten.

8. A process as claimed in claim 1, wherein the hydrogenation catalyst used in step c) of the process is a catalyst comprising at least one transition metal selected from the group of copper, silver, iron, cobalt, nickel, ruthenium, rhodium, palladium, osmium, iridium and platinum.

9. A process as claimed in claim 1, wherein the hydrogenation catalyst used in step c) of the process is a catalyst comprising at least one transition metal selected from the group of copper, cobalt, nickel, ruthenium, iridium, rhodium, palladium and platinum.

10. A process as claimed in claim 2, wherein the IPDA is separated in step b) of the process into a fraction having a cis/trans isomer ratio in the range from 73/27 to 76/24 and a fraction having a cis/trans isomer ratio of less than 63/37.

11. A process as claimed in claim 3, wherein the IPDA is separated in step b) of the process into a fraction having a cis/trans isomer ratio in the range from 73/27 to 76/24 and a fraction having a cis/trans isomer ratio of less than 63/37.

12. A process as claimed in claim 4, wherein the IPDA is separated in step b) of the process into a fraction having a cis/trans isomer ratio in the range from 73/27 to 76/24 and a fraction having a cis/trans isomer ratio of less than 63/37.

13. A process as claimed in claim 2, wherein crude IPDA having a cis/trans isomer ratio of $\leq 70/30$ is provided in step a) of the process.

14. A process as claimed in claim 3, wherein crude IPDA having a cis/trans isomer ratio of $\leq 70/30$ is provided in step a) of the process.

15. A process as claimed in claim 4, wherein crude IPDA having a cis/trans isomer ratio of $\leq 70/30$ is provided in step a) of the process.

16. A process as claimed in claim 5, wherein crude IPDA having a cis/trans isomer ratio of $\leq 70/30$ is provided in step a) of the process.

17. A process as claimed in claim 2, wherein the hydrogenation catalyst used in step c) of the process is a catalyst comprising at least one transition metal selected from the group of copper, silver, gold, iron, cobalt, nickel, rhenium, ruthenium, rhodium, palladium, osmium, iridium, platinum, chromium, molybdenum and tungsten.

18. A process as claimed in claim 3, wherein the hydrogenation catalyst used in step c) of the process is a catalyst comprising at least one transition metal selected from the group of copper, silver, gold, iron, cobalt, nickel, rhenium, ruthenium, rhodium, palladium, osmium, iridium, platinum, chromium, molybdenum and tungsten.

19. A process as claimed in claim 4, wherein the hydrogenation catalyst used in step c) of the process is a catalyst comprising at least one transition metal selected from the group of copper, silver, gold, iron, cobalt, nickel, rhenium, ruthenium, rhodium, palladium, osmium, iridium, platinum, chromium, molybdenum and tungsten.

20. A process as claimed in claim 5, wherein the hydrogenation catalyst used in step c) of the process is a catalyst comprising at least one transition metal selected from the group of copper, silver, gold, iron, cobalt, nickel, rhenium, ruthenium, rhodium, palladium, osmium, iridium, platinum, chromium, molybdenum and tungsten.

* * * * *